US006821417B2

United States Patent
Yang et al.

(10) Patent No.: US 6,821,417 B2
(45) Date of Patent: Nov. 23, 2004

(54) CHROMATOGRAPHIC AND ELECTROPHORETIC SEPARATION OF CHEMICALS USING ELECTRICALLY CONDUCTIVE POLYMERS

(75) Inventors: Sze Cheng Yang, Wakefield, RI (US); Phyllis R. Brown, Saunderstown, RI (US); Christina S. Robb, Kingston, RI (US); Patrick McCarthy, St. Paul, MN (US)

(73) Assignee: The Board of Governors, State of Rhode Island and Providence Plantations, Providence, RI (US)

(*) Notice: Subject to any disclaimer, the term of this patent is extended or adjusted under 35 U.S.C. 154(b) by 118 days.

(21) Appl. No.: 10/191,683

(22) Filed: Jul. 9, 2002

(65) Prior Publication Data

US 2003/0080057 A1 May 1, 2003

Related U.S. Application Data

(63) Continuation of application No. PCT/US01/00973, filed on Jan. 11, 2001.
(60) Provisional application No. 60/175,700, filed on Jan. 12, 2000.

(51) Int. Cl.$^7$ .............................................. B01D 15/08
(52) U.S. Cl. ................................ 210/198.2; 210/502.1; 210/635; 210/656; 210/748; 210/243; 252/500
(58) Field of Search ................................. 210/635, 656, 210/659, 198.2, 502.1, 748, 243; 252/500

(56) References Cited

U.S. PATENT DOCUMENTS

| 5,225,495 A | 7/1993 | Han et al. .................... 525/327 |
| 5,547,581 A | 8/1996 | Andelman ................ 210/198.2 |
| 6,150,032 A | 11/2000 | Yang et al. .................. 252/500 |
| 6,656,388 B1 * | 12/2003 | Yang et al. .................. 252/500 |

FOREIGN PATENT DOCUMENTS

| WO | WO 89/07265 | 3/1989 | .............. 210/198.2 |
| WO | WO 94/00215 | 6/1993 | .............. 210/198.2 |

* cited by examiner

*Primary Examiner*—Ernest G. Therkorn
(74) *Attorney, Agent, or Firm*—Gauthier & Connors LLP

(57) ABSTRACT

A separation system comprising a stationary phase, a double stranded conductive polymer system contacting the stationary phase and means to place a mobile phase carrying a component to be separated from the mobile into contacting relationship with the polymer system whereby the component is captured by the polymer. The double stranded polymer is comprised of a -conjugated polymer and a polyelectrolyte.

8 Claims, 6 Drawing Sheets

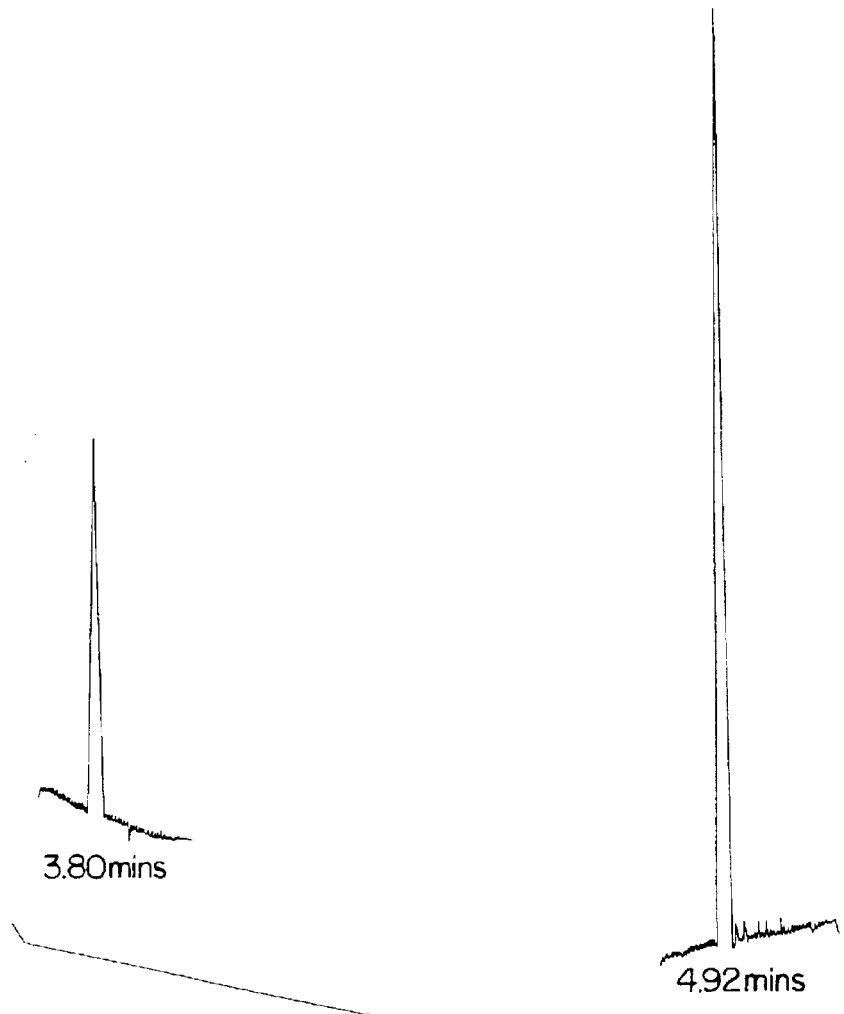
FIG. IA
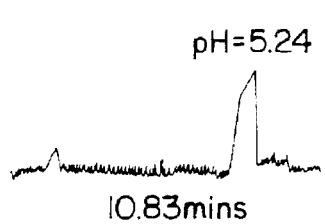
FIG. IB

CHROMATOGRAPHIC AND ELECTROPHORETIC SEPARATION OF CHEMICALS USING ELECTRICALLY CONDUCTIVE POLYMERS

CROSS REFERENCE TO RELATED APPLICATIONS

This application is a continuation of PCT/US01/00973 filed Jan. 11, 2001.

This application claims the benefit of U.S. Provisional Application No. 60/175,700, filed Jan. 12, 2000.

BACKGROUND OF THE INVENTION

1. Field of the Invention

This invention relates to the synthesis and use of double stranded polymers to separate chemical mixtures.

2. Description of the Related Art

The ability to separate chemical mixtures into their individual components is a billion dollar industry. Speed, resolution, efficiency, reproducibility, repeatability and low cost are all factors that determine a good separation method. Current methods to separate chemical mixtures include chromatography and electrophoresis. These techniques are essential for clinical analysis, for biotechnology, environmental analysis, and for drug development. Chemical separation primarily entails the chemical/physical interaction of a stationary surface (a stationary phase) with chemicals (in a mobile phase) that flow by the surface of the stationary phase.

Chromatography achieves the separation of chemical mixtures by the use of a mobile phase and a stationary phase. The mixture is injected into the mobile phase and the mobile phase then flows over the stationary phase. The different interactions of the individual components with this combination of phases creates a separation. If a neutral component has a polar character then it will be retained longest by a polar stationary phase. Neutral non-polar solutes will be retained best by a non-polar stationary phase. The mobile phase can be liquid, a gas or a supercritical fluid. The stationary phase can be a packed or wall coated standard or capillary column. The type of mobile phase determines the name of the method, e.g. liquid chromatography, gas chromatography . . . etc.

A conductive polymer, namely single strand polyaniline, has been coated on a glassy carbon stationary phase to achieve charge controlled chromatography. The coating allowed the number of ion exchange sites in the stationary phase to be controlled instead of being fixed as in ion chromatography and inorganic anions and organic acids were separated. However, a drawback of coating the single strand polyaniline on the stationary phase is that the single strand polyaniline does not have a wide enough pH range to be usable.

Electrophoresis creates separations of charged molecules. Electrophoresis is principally used for the separation of biological molecules and remains a standard biological tool. Charged molecules can be separated in slab gels by the application of an electric field. Capillary electrophoresis separates charged molecules according to their electrophoretic mobilities in an electric field. Generally, the separation compartment is a narrow fused silica capillary filled with an electrolyte solution. The electric field is applied with an external voltage source between two electrodes in small vials in contact with the electrolyte solution at both ends of the capillary. The sample is introduced either hydrostatically or electro migration as a narrow zone at one end of the capillary. Typically, UV detection takes place at the other end of the capillary.

Fused silica is the typical capillary material used in capillary electrophoresis because it is inexpensive, easy to fabricate into capillaries with internal diameters in the 10–300$\mu$m ranges, possesses optical transparency for both UV and visible spectrums, is mechanically strong and is flexible when coated with polyimide. However, the material properties of fused silica presents some drawbacks when used in capillary elecrophoresis. For example, the surface silanol groups of the fused silica behave as a weak acid, ionizing in water, with a broad titration curve in the pH 3.9 to 9 region. These surface anionic groups induce both electro osmotic flow (EOF) and solute wall interactions to occur. Solute wall interactions typically occur with cationic proteins that electrostatically bind to the silica. Reversible interactions between such analytes and the capillary surface worsen the separation profile, broadening the peaks and decreasing reproducibility, while irreversible interactions can destroy the flow profile entirely. Attempts to reduce these interactions include the use of extreme pH buffers (very high and very low), the use of additives and modification of the capillary surface.

Several coatings have been applied to the surfaces of a capillary to address the drawbacks associated with the use of fused silica as the capillary material in capillary electrophoresis. For example, nonconducting polymers have been adsorbed to the surface of a fused silica capillary. However, the prior art polymeric coatings that have been adsorbed to the surface of a fused silica capillary are typically unstable.

The present invention provides a coating for the stationary phase of a chemical separation system, the coating comprising a double stranded conductive polymer that is efficient, effective and overcomes the drawbacks associated with existing chemical separation systems.

BRIEF SUMMARY OF THE INVENTION

Broadly, the invention comprises a double stranded conductive polymer functioning as the stationary phase of a chemical and/or biological separation system. The double stranded conductive polymer provides controllable interactions between the polymer system of the stationary phase and the chemicals and/or biological analyte in a carrier stream. The invention further comprises a chemical separation system comprised of stationary phase comprising a double stranded polymer.

The double stranded conductive polymer used in the invention comprises a linear strand of polyaniline and a linear strand of a polyelectrolyte twisted together to form a macro-molecule. The polyaniline strand can be modified to predictably change its hydrophobicity and/or its color when the pH and/or the electrochemical potential within the separation system is changed. The modification of the polyaniline strand controls the analyte-surface interactions to improve the separation. The linear strand of polyelectrolyte provides the properties suitable for non-aggressive interactions with the analyte or carrier stream.

The double stranded conductive polymers can be used as a part of the stationary phase in a chromatographic column, as a coating on the inner surface of a capillary for separation by capillary electrophoresis, as part of a filtration membrane, as a component in gel electrophoresis and/or coated on or admixed with particulate material packed in a column or the like. The double stranded conductive polymer has the chemical structure that is suitable for selective interaction with molecules dissolved in a carrier fluid that flows by the polymer to effect chemical separation of the components in the mixture.

The double stranded conductive polymers used for chemical separation belong to a class of polymers comprising a molecular complex of two strands of polymers: (1) a π-conjugated polymer such as polyaniline, plypyrrole, polythiophen, poly(phenylene vinylene), etc. and (2) a polyelectrolyte such as poly(acrylic acid), poly(methylvinylether-co-maleic acid), poly(butadiene-co-maleic acid), poly(vinylsulfonic acid), poly(styrenesulfonic acid), poly(methacrylic acid), poly(L-glutamic acid), poly(L-Asparic acid), etc. The two strands of the molecular complex are bonded non-covalently for most of the applications, although crosslinking between the two strands is also possible. The synthetic process (the template-guided synthesis) allows the control of solubility, conformation, and the morphology of the polymer and thus provides advantageous properties for chemical separation applications. The two strands of polymers in the molecular complex are likely to be non-covalently bonded in a side-by-side arrangement thus they are referred to as double-stranded polymers, although the actual structure of the complex could be somewhat random.

A double stranded conductive polymer was coated on the inner surface of a glass capillary in a capillary electrophoretic separation apparatus. The electro osmotic flow (EOF) carried the chemical mixture through the capillary. Due to the influence of the π-conjugated polymers coated on the capillary wall, the different types of molecules in the mobile phase are separated by their difference in elution time. The present invention embodies coatings for improving the analysis of organic and inorganic species by chromatographic and electrophoretic techniques. These experiments demonstrate the beneficial molecular interaction between the stationary and the mobile phases. The same molecular interactions can be used for liquid chromatography, HPLC, of thin-layer chromatography for chemical analysis. The double stranded conductive polymers are also useful for large-scale separation of chemicals or drugs when it is used as a component in preparative-scale chromatography or as part of a membrane for selective filtration of chemicals.

The double stranded polymer used for the preferred embodiment comprises two components: (1) a polyaniline molecule, and (2) a polyanion. These two strands of polymers are bonded by non-covalent intermolecular interactions to form a stable molecular complex. Examples of the polyanion in the polymeric complexes are poly(stryrenesulfonic acid), poly(acrylic acid), poly(methacrylic acid), poly(2-acryamido-2-methyl-1-propenesulfonic acid), and poly(methylacrylate-co-acrylic acid), poly(butadiene-co-maleic acid), poly(glutamic acid), poly(aspartic acid), etc.

Another advantage of using the double stranded conductive polymers in a chemical separation system is the relative ease in functionalizing the polymer to adjust material properties to meet the demand for practical applications. The double stranded conductive polymers are synthesized to be soluble in water, or soluble in organic solvents, or suspended in latex to satisfy the demands of coatings applications. Certain functional groups of the double stranded conductive polymer provide strong adhesion to metals and other polymers, an advantageous property for coatings application for the stationary phase in the separation system.

The double-strand conductive polymers are synthesized by a method that encourages the formation of molecular complexes. In the first step, aniline monomers are absorbed onto a polyanion chain dissolved in solution. The resulting adduct, polyanion:(aniline)$_x$ has signatures that can be monitored and verified. In the second step, the attached aniline monomers are oxidatively polymerized to form the polymeric complex.

The adduct of polyanion:(aniline)$_x$ may take the shape of a tight coil or extended chains. The shape of the adduct controls the morphology of the polymerized product. A tight-coiled adduct results in globular polyaniline complex, while an extended chain adduct results in thin fibers of the double-strand complex aggregates (100 nm diameter×5 micron length). Thus the polyanion functions as a template during the chemical synthesis, and the template becomes the second strand of the "double-strand" polyaniline after polymerization.

That is the template guided synthesis allows for controlling the morphology (e.g., fibrous or globular) of the complex as well as the conformation (e.g., coiled or extended chain, helical or sheet conformation) of the polymer. Because the polymer has delocalized electrons on the polymer backbone, the van der Waals and electrostatic interaction of the polymer with the mobile phase can be quite different from the conventional materials for stationary phase. This feature is advantageous for separation of proteins, DNA, and drugs because the delocalized binding between the polymer and the analytes can be designed to be specific enough to be selective among the molecules that are otherwise difficult to be separated.

BRIEF DESCRIPTION OF THE DRAWING(S)

FIG. 1A depicts electropherograms for iodide anions on an uncoated capillary.

FIG. 1B depicts electropherograms for iodide anions on a coated capillary.

DESCRIPTION OF THE PREFERRED EMBODIMENT(S)

Figure 2A:
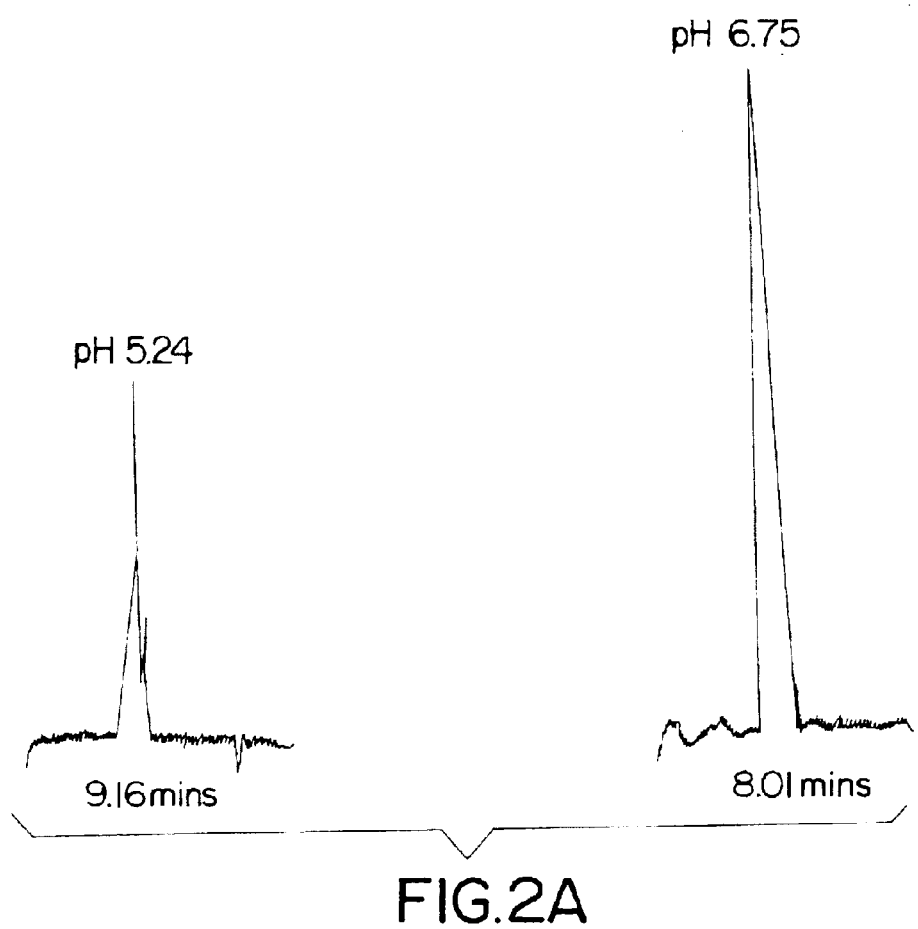
FIG. 2A depicts electropherograms for bromide anions on an uncoated capillary.

In the preferred embodiment of the invention, the double stranded conductive polymer system, which is applied to or, alternatively, comprises the stationary phase of the chemical separation system, is polyaniline: polymethylmethacrylate. The synthesis of polyaniline: polymethylmethacrylate (PANI: PMMA) disclosed herein is disclosed in International Application No. PCT/US96/11646, entitled "Electroactive Polymer Coatings for Corrosion Control" and the same is incorporated by reference in its entirety into this disclosure.

Tempate-guided Synthesis of Double-strand Polyaniline:poly(acrylic Acid-co-methylacrylate)

Step I

The mole ratio between the carboxylic acid groups and the aniline monomer units ranged from 2:1 to 1:1. The resulting polymeric complex was soluble or dispersable in water, methanol and ethanol. The procedure for synthesis of polyaniline:poly(acrylic acid) complex has been reported supra and the reported procedures were followed.

Step II

The polyaniline:poly(acrylic acid) complex prepared in step 1 was dissolved in methanol. To this solution is added catalytic amount of benzene suflonic acid or toluene sulfonic acid to serve as a catalyst for esterification reaction. The solution was refluxed for 3 days. The esterification reaction converted some of the carboxylic acid group into the methyl acetate group. This lowered the solubility of the complex in methanol and the polymeric complex precipitated out of the solution. The precipitate was filtered out and dissolved in ethyl acetate. If a higher degree of esterification was desired, the precipitate could be redissolved in 1:1 mixture of ethylacetate and methanol, and the solution further refluxed until precipitate was again formed. This precipitate was soluble in pure ethyl acetate but is not soluble 1:1 mixture of ethyl acetate and methanol.

Coating Procedures

Two coating procedures where employed using the PANI:PMMA double stranded conductive polymer.

Procedure 1

A dilute solution of the polymer in ethyl acetate was pushed through a fused silica capillary. (The capillary(s) used were polyimide coated fused silica 100 to 300 mm inner diameter). A small amount of the polymer was sealed in a vial and the end of the capillary pushed through the seal. An air filled syringe was also pushed through the seal. When the syringe was depressed the air displaced the polymer solution and the solution flowed through the capillary. The polymer could be seen exiting the other end of the capillary and so it was known that the solution was being pushed through the capillary. After a few minutes, air was pushed through the capillary in the same manner to remove the excess polymer from the capillary.

Procedure 2

The second procedure was more exact. The concentration of the polymeric solution was determined to be approximately 2.1 g/L. The solution was diluted in ethyl acetate to produce a solution that was 0.1% in ethyl acetate. The capillary was pretreated (to clean the surface) by washing it with 0.1M sodium hydroxide for 30 minutes followed by 0.1M hydrochloric acid for another 30 minutes. Finally, it was rinsed with distilled water for 30 minutes. The capillary was then heated in a nitrogen atmosphere at 100° C. for 2 hours to dry the coating. The capillary was cooled before use. A comparison was made of the readings on the UV spectrometer (at 214 nm) after each stage of the coating procedure and it was noted that the presence of the coating could be detected by the spectrometer.

The invention will further be described with reference to the following non-limiting examples.

EXAMPLE I

Iodide and Bromide Anions

Initial tests of the coating were performed using iodide and bromide anions. These were chosen as the model compounds because they are simple, charged compounds, which absorb in the UV region.

Separation Conditions

Results

TABLE 1

Results for iodide and bromide anions

| | IODIDE pH 5.25 | IODIDE pH 6.75 | BROMIDE pH 5.25 | BROMIDE pH 6.75 |
|---|---|---|---|---|
| UNCOATED CAPILLARY (MIGRATION TIME minutes) | 3.80 | 4.92 | 4.19 | 5.09 |
| COATED CAPILLARY (MIGRATION TIME minutes) | 10.83 | 7.71 | 9.16 | 8.01 |

Referring to FIGS. 1A, 1B and Table 1, the coating was present on the capillary surface as illustrated by the differences obtained on the uncoated and coated capillaries. An increase in pH was accompanied by an increase in migration time for the bare capillary and a decrease in migration for the coated capillary. The coating affects the elution of anions in the capillary and the coating was changing with the pH of the solution.

EXAMPLE II

Monophosphate Nucleotides

The use of PANI: PMMA as a coating for a capillary in capillary electrophoresis is present and effective for the analysis of small, biological molecules. The following results reveal the effect of pH and buffer concentration on the coated capillary and the effectiveness of pre-treating the fused silica capillary as part of the coating procedure.

Separation Conditions

The capillaries were coated using procedure 2. The separation conditions were +20 kV, a 20Mm acetate buffer, an injection time of 10s and the separation was performed on a Waters Quanta capillary electrophoreses system.

Results

TABLE 2

Electroosmotic flow comparison for coated and uncoated capillaries at a pH of 4

| | ELECTROOSMOTIC FLOW |
|---|---|
| UNCOATED CAPILLARY | $2.89 \times 10^{-4}$ |
| COATED CAPILLARY | $6.31 \times 10^{-4}$ |

TABLE 3

Migration time comparison for coated and uncoated capillaries at a pH of 4

| | MIGRATION TIME ON COATED CAPILLARY | MIGRATION TIME ON UNCOATED CAPILLARY |
|---|---|---|
| CMP | 11.45 minutes | 5.30 minutes |
| AMP | 14.35 minutes | 5.45 minutes |
| GMP | 17.66 minutes | 5.60 minutes |
| UMP | 19.89 minutes | 5.80 minutes |

Figure 2B:
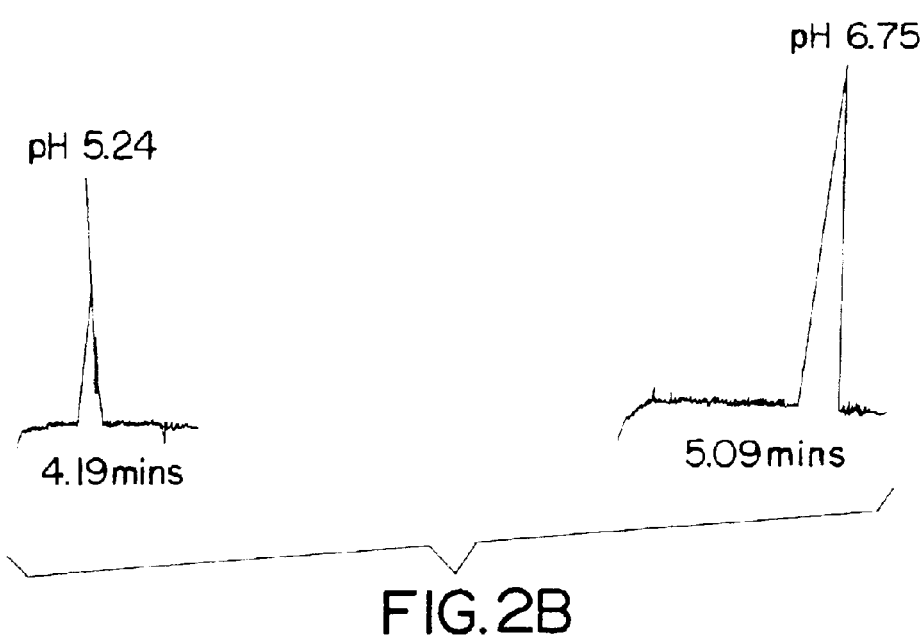
FIG. 2B depicts electropherograms for bromide anions on a coated capillary.
Figure 3A:
FIG. 3A depicts an electropherogram for nucleotides at a pH of 6 on a coated capillary.
Figure 3B:
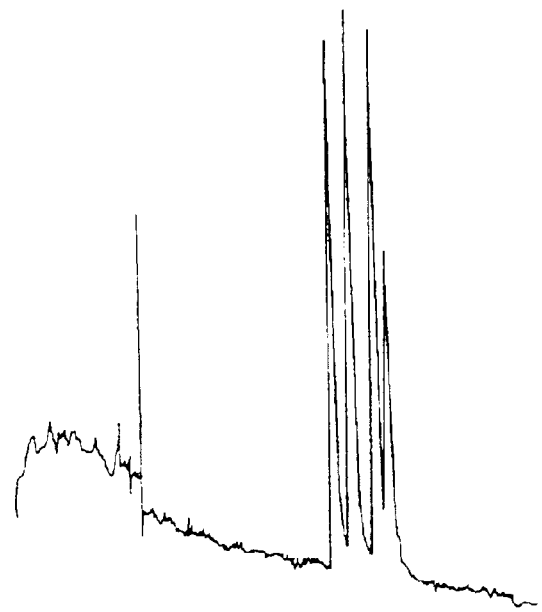
FIG. 3B depicts an electropherogram for nucleotides at a pH of 6 on an uncoated capillary.
Figure 4A:
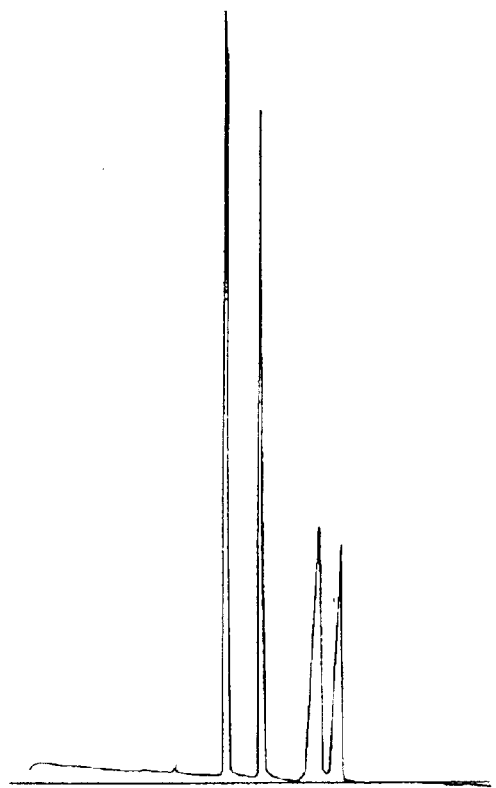
FIG. 4A depicts an electropherogram for nucleotides at a pH of 7 on a coated capillary.
Figure 4B:
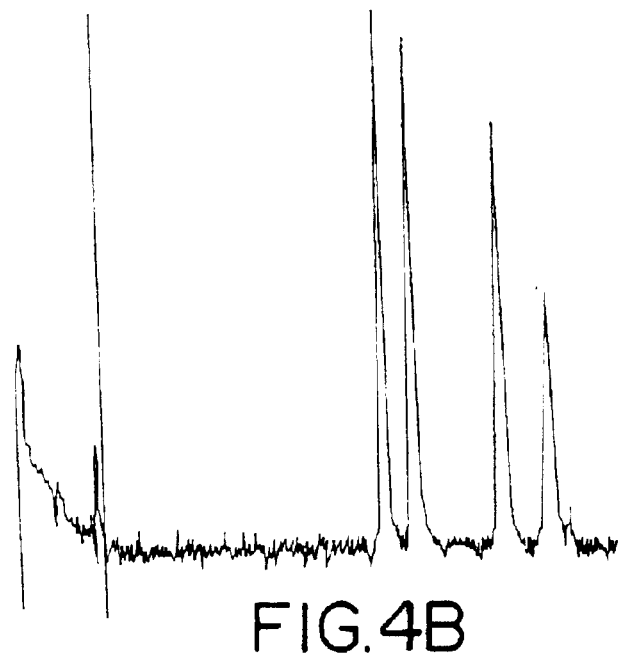
FIG. 4B depicts an electropherogram for nucleotides at a pH of 7 on an uncoated capillary.
Figure 5A:
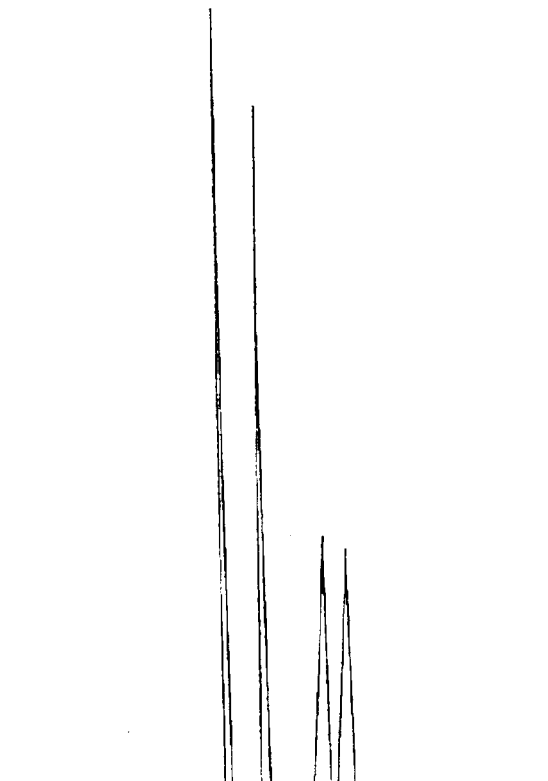
FIG. 5A depicts an electropherogram of nucleotides (50 Mm acetate buffer, at a pH of 4).
Figure 5B:
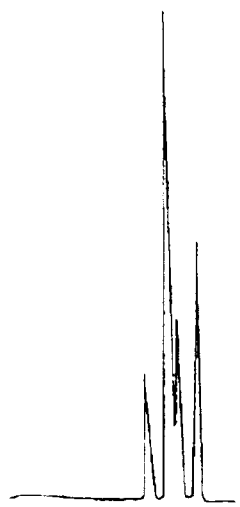
FIG. 5B depicts an electropherogram of nucleotides (20 Mm acetate buffer, at a pH of 4).

Referring to FIGS. 2A, 2B, Table 2 and Table 3, when the same nucleotide samples were run on both a PANI: PMMA coated capillary and an uncoated fused silica capillary under the same conditions, significant changes in the separation were attained signaling the presence of the PANI: PMMA coating. The EOF values for the capillaries reveal that the coated capillary is significantly faster than the uncoated capillary. Using a bare capillary it was not possible even under optical conditions of high pH to separate monophosphate nucleotides in such a short amount of time. This constitutes a rapid analysis technique. The migration window was also observed to be much shorter than that of the uncoated capillary.

Additional tests were performed to observe the influence of pH on the coated capillaries. In both cases the separation attained on the coated capillary is accompanied by the separation attained on the uncoated capillary.

Separation Conditions

The capillaries were coating using procedure 1. The separation conditions were +20 kV, a 50Mm phosphate buffer, an injection time of 10s and the separation was performed on a Waters Quanta capillary electrophoresis system.

Results

TABLE 4

Migration time comparison for coated capillaries at a pH of 6 and a pH of 7

|  | MIGRATION TIME ON COATED CAPILLARY at a pH of 6 | MIGRATION TIME ON COATED CAPILLARY at a pH of 7 |
|---|---|---|
| CMP | 18.20 minutes | 18.00 minutes |
| AMP | 19.51 minutes | 16.31 minutes |
| GMP | 20.34 minutes | 15.00 minutes |
| UMP | 21.00 minutes | 19.12 minutes |

TABLE 5

Migration time comparison for uncoated capillaries at a pH of 6 and a pH of 7

|  | MIGRATION TIME ON UNCOATED CAPILLARY | MIGRATION TIME ON UNCOATED CAPILLARY |
|---|---|---|
| CMP | 17.50 minutes | 41.00 minutes |
| AMP | 16.00 minutes | 30.25 minutes |
| GMP | 18.22 minutes | 5.60 minutes |
| UMP | 19.21 minutes | 38.27 minutes |

Referring to FIGS. 3A, 3B, 4A, 4B, Table 4 and Table 5, the migration order differences of the nucleotides in the coated and uncoated capillaries revealed the presence of the coating and the difference in behavior between the coating and fused silica. It can be seen that there is a large difference in migration times for the capillaries at a pH of 7 and that the coated capillary presents a large advantage at this pH. The two capillaries were the same size and the difference cannot be attributed to any feature other than the presence of the coating.

Additional experiments were performed to reveal the what effect the coated capillaries had at different concentrations of the same buffer differences in the migration times of the monophosphate nucleotides are noted. The initial analysis was all performed with a high concentration buffer (50 mM) but later analysis was also performed at 20Mm.

Separation Conditions

The samples were run on the Water's Quanta capillary electrophoresis instrument. An injection time of 10 seconds and a running voltage of 20 kV were used. Acetate buffer at the two different concentrations was prepared by the same method. The capillary equilibrated at each concentration for about 40 minutes before the samples were injected.

TABLE 6

Migration time comparison for coated capillaries at a pH of 4 and different concentrations

|  | MIGRATION TIME ON COATED CAPILLARY with 50 Mm buffer | MIGRATION TIME ON COATED CAPILLARY with 20 Mm buffer |
|---|---|---|
| CMP | 9.25 minutes | 5.30 minutes |
| AMP | 11.13 minutes | 5.45 minutes |
| GMP | 14.35 minutes | 5.60 minutes |
| UMP | 15.12 minutes | 5.80 minutes |

Results

The coating can be seen to respond to the difference in buffer concentration. The response was highly reproducible. It can be observed that the lower concentration of buffer gives the faster analysis. It can be concluded that at low pH the coating appears to produce excellent separations of nucleotides. It enhances the separations attained by the uncoated capillaries considerably.

EXAMPLE III

Proteins

Example II illustrate the ability of the coating to separate, small, biological molecules in a fast, efficient and reproducible manner. The following example illustrates the ability of the coating to separate, large, biological molecules, such as proteins, in a fast, efficient and reproducible manner. A mixture of albumin and glyceraldehydes was prepared and analyzed.

Separation Conditions

The analysis was performed with a 20 Mm borate buffer at a pH of 8, injection time of 20 seconds and an applied voltage of +15 kV.

Results

TABLE 7

Efficiency values for albuim on the coated and uncoated capillary

|  | EFFICIENCY ON COATED CAPILLARY | EFFICIENCY ON UNCOATED CAPILLARY |
|---|---|---|
| ALBUMIN | 179496 THEORETICAL PLATE NUMBERS | 14652 THEORETICAL PLATE NUMBERS |

Coating capillary increased efficiency by one order of magnitude.

Figure 6A:
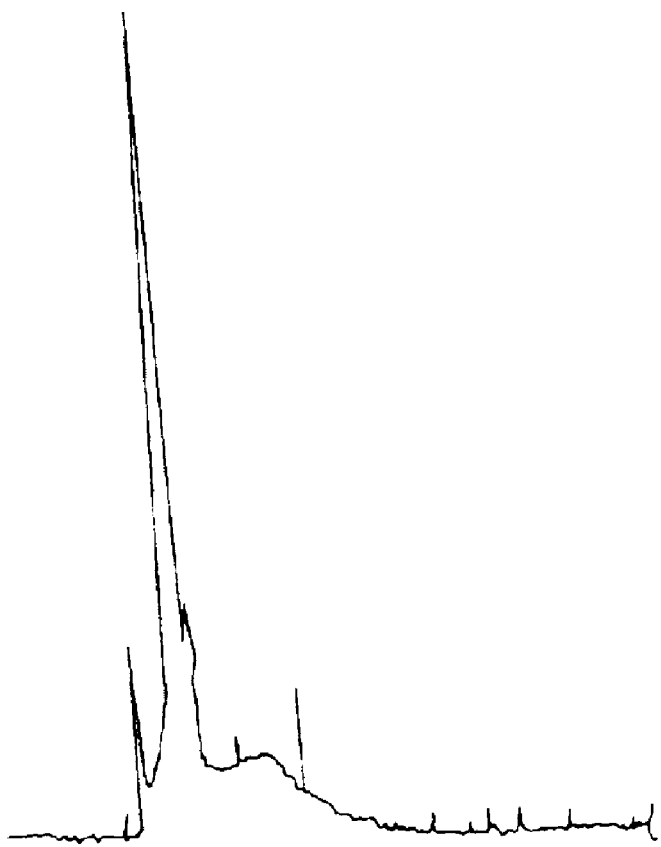
FIG. 6A depicts an electropherogram of albumin and glyceraldehydes on a coated capillary.
Figure 6B:
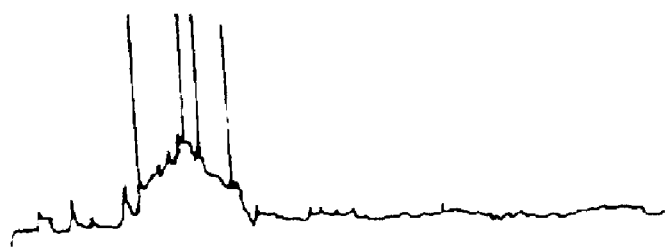
FIG. 6B depicts an electropherogram of albumin and glyceraldehydes on an uncoated capillary.

Referring to FIGS. 6A, 6B and Table 7 and in regard to the protein analysis on the uncoated capillary, the protein appears to have not eluted and is most likely adhered to the wall of the capillary. Using the coated capillary the protein is seen to elute with good peak shape and in a relatively short amount of time.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A separation system comprising:

a stationary phase;

a double stranded conductive polymer system contacting the stationary phase; and means to place a mobile phase carrying a component into contacting relationship with the polymer, the polymer predictably affecting the movement of the component within the mobile phase when the mobile phase flows by at least a portion of the stationary phase.

2. The separation system according to claim 1 wherein the double stranded conductive polymer system is comprised of a π-conjugated polymer and a polyelectrolyte.

3. The separation system according to claim 2 wherein the π-conjugated polymer is selected from the group consisting of polyaniline, plypyrrole, polythiophene, and poly (phenylene vinylene).

4. The separation system according to claim 2 wherein the polyelectrolyte is selected from the group consisting of poly(acrylic acid), poly(methylvinylether-co-maleic acid), poly(butadiene-co-maleic acid), poly(vinylsulfonic acid), poly(styrenesulfonic acid), poly(methacrylic acid), poly(L-glutamic acid), poly(L-Asparic acid), and poly (methylacrylate-co-acrylic acid).

5. The system according to claim 1 wherein the stationary phase is selected from the group consisting of particulate materials, porous materials, semi-sold materials and solid materials.

6. The system according to claim 1 wherein the stationary phase is a fused silica capillary.

7. The system according to claim 1 wherein the mobile phase is a liquid or a gas.

8. The system according to claim 1 wherein the component is a macromolecule.

* * * * *